United States Patent [19]

Mauldin et al.

[11] Patent Number: 4,572,169
[45] Date of Patent: Feb. 25, 1986

[54] REMOVABLE LOWER LEG BRACE

[75] Inventors: Donald M. Mauldin; Richard E. Jones, III, both of Dallas, Tex.

[73] Assignees: Kenneth D. Driver, Memphis, Tenn.; Melvin L. Stills, Lewisville, Tex.

[21] Appl. No.: 596,292

[22] Filed: Apr. 3, 1984

[51] Int. Cl.$^4$ .............................................. A61F 3/00
[52] U.S. Cl. ................................................ 128/80 H
[58] Field of Search ............... 128/80 H, 80 R, 166, 128/80 E, 80 F, 83, 165, 89 R, 87 R, 84 R

[56] References Cited

U.S. PATENT DOCUMENTS

| | | |
|---|---|---|
| 1,575,042 | 3/1926 | Denniston . |
| 2,278,626 | 4/1942 | Vasko . |
| 2,317,020 | 4/1943 | Banister . |
| 2,341,963 | 2/1944 | Telson . |
| 2,404,083 | 7/1946 | Murray . |
| 2,410,560 | 11/1946 | Witte . |
| 2,423,354 | 7/1974 | Van Hoesen . |
| 2,614,340 | 10/1952 | Larkin . |
| 2,725,648 | 12/1955 | Kirk et al. . |
| 2,733,522 | 2/1956 | Murray . |
| 2,762,367 | 9/1956 | Rubin . |
| 2,810,213 | 10/1957 | Jonas . |
| 2,875,752 | 3/1959 | Lovich . |
| 2,884,717 | 3/1959 | Goldberg . |
| 3,044,463 | 7/1962 | Cool . |
| 3,307,536 | 3/1967 | Blosser . |
| 3,545,104 | 12/1970 | Laurie . |
| 3,566,487 | 3/1971 | Beightol . |
| 3,613,674 | 10/1971 | Volz . |
| 3,633,573 | 1/1972 | Lipson . |
| 3,732,861 | 3/1973 | Lehneis . |
| 3,802,424 | 4/1974 | Newell . |
| 3,805,773 | 4/1974 | Sichau . |
| 3,814,088 | 6/1974 | Raymond . |
| 3,884,402 | 6/1971 | Silverman . |
| 3,905,135 | 9/1975 | Debusk . |
| 4,166,460 | 9/1979 | Applegate . |
| 4,178,925 | 12/1979 | Hirt . |
| 4,200,997 | 5/1980 | Scheinhaus . |
| 4,217,893 | 8/1980 | Payton . |
| 4,280,489 | 7/1981 | Johnson, Jr. . |
| 4,320,748 | 3/1982 | Racette et al. . |
| 4,378,793 | 4/1983 | Mauldin et al. ............ 128/80 H |
| 4,414,965 | 11/1983 | Mauldin et al. . |

Primary Examiner—John D. Yasko
Assistant Examiner—Christa K. Scott
Attorney, Agent, or Firm—Cox & Smith Inc.

[57] ABSTRACT

A removable ankle brace (10) comprises a rigid shoe (14), side members (16) extending upwardly from both sides of the rigid shoe and side plates (18) extending upwardly from the side members. The rigid shoe (14) comprises a molded plastic body portion (50). The side members (16) are formed integrally with the molded plastic body portion (50) thereby preventing relative motion therebetween. A brace for tibial fractures (110) is constructed similarly to the removable ankle brace, but includes an extension (112) secured to the side plates (18') and extending upwardly therefrom.

10 Claims, 6 Drawing Figures

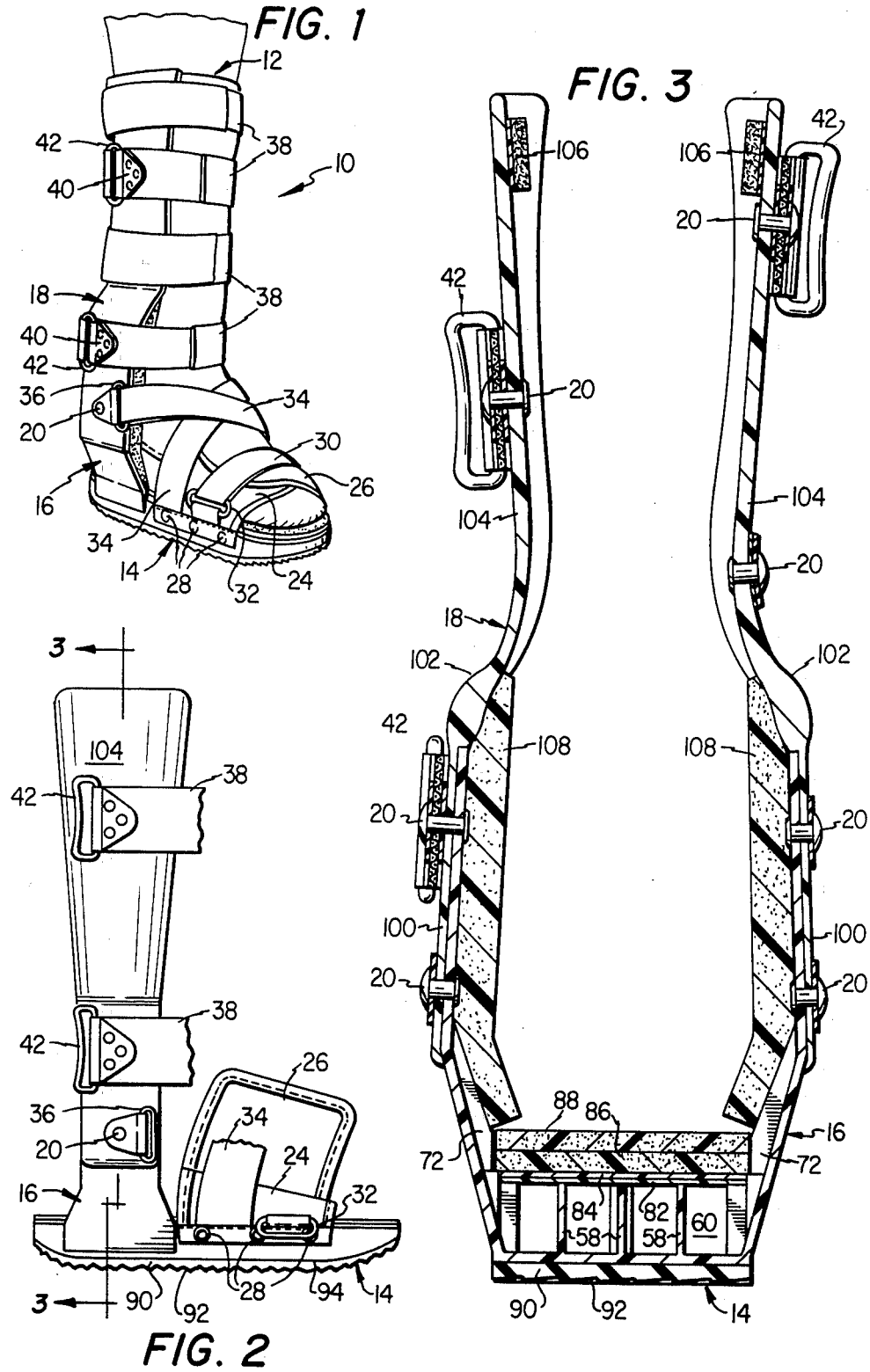

4,572,169

REMOVABLE LOWER LEG BRACE

TECHNICAL FIELD

This invention relates generally to braces for use in the medical treatment of the lower portion of the human leg, and more particularly to an angle brace having a molded plastic body portion.

BACKGROUND AND SUMMARY OF THE INVENTION

U.S. Pat. No. 4,378,793 granted to Donald M. Mauldin and Richard E. Jones, III on Apr. 5, 1983 discloses a Removable Ankle Brace. U.S. Pat. No. 4,414,965 granted to Mauldin and Jones on Nov. 15, 1983 discloses a Brace For Tibial Fractures. Both of the prior Mauldin-Jones devices employ a rigid shoe comprising a wooden body portion. Side members extend upwardly from both sides of the rigid shoe and are secured to the wooden body portion thereof by means of threaded fasteners.

Although the braces disclosed in the above-identified patents have achieved considerable commercial success, certain difficulties have been observed in the use thereof. In particular, it has been found that after extended use, the fasteners that secure the side members to the wooden body portion of the rigid shoe tend to loosen. This can lead to the possibility of relative movement between the side members and the rigid shoe. Since the proper functioning of the brace requires absolute stability between the side members and the rigid shoe, it will be understood that loosening of the fasteners which secure the side member to the rigid shoe necessitates either the repair or the replacement of the brace. Thus, a need exists for an improved brace structure which retains the beneficial characteristics of the prior Mauldin-Jones devices, but which eliminates any possibility of relative movement between the side members and the rigid shoe even after extended service.

The present invention fulfills the foregoing requirements to provide a substantially improved brace structure that is highly useful in the medical treatment of the lower portion of the human leg. The brace comprises a rigid shoe which is characterized by a molded plastic body portion. Molded plastic side members are formed integrally with the molded plastic body portion and extend upwardly from both sides thereof. This eliminates any possibility of relative movement between the side members and the rigid shoe of the brace.

In accordance with a first embodiment of the invention, the molded plastic body portion of the rigid shoe comprises a bottom wall and a side wall extending around the periphery of the bottom wall. Longitudinally and transversely disposed ribs extend upwardly from the bottom wall to a plane lying beneath the upper edge of the side wall. An inner sole having a double thickness in the heel region is supported by the ribs and in turn supports foam layers which receive the foot of the patient. The molded plastic side members extend upwardly from the side walls of the molded plastic body portion on opposite sides thereof and are provided with vertically disposed reinforcing ribs. Molded plastic side pieces are secured to the molded plastic side members by suitable fasteners and extend upwardly therefrom. In accordance with a second embodiment of the invention, an extension is secured to the side pieces for use in treating tibial fractures.

DESCRIPTION OF THE DRAWINGS

A more complete understanding of the invention may be had by reference to the following Detailed Description when taken in conjunction with the accompanying Drawings, wherein:

FIG. 1 is a perspective view of a removable ankle brace incorporating a first embodiment of the invention showing the brace properly mounted on the lower leg of a patient;

FIG. 2 is a side view of the removable ankle brace of FIG. 1;

FIG. 3 is a sectional view of the removable ankle brake taken generally along the line 3—3 in FIG. 2 in the direction of the arrows;

DETAILED DESCRIPTION

Figure 5:
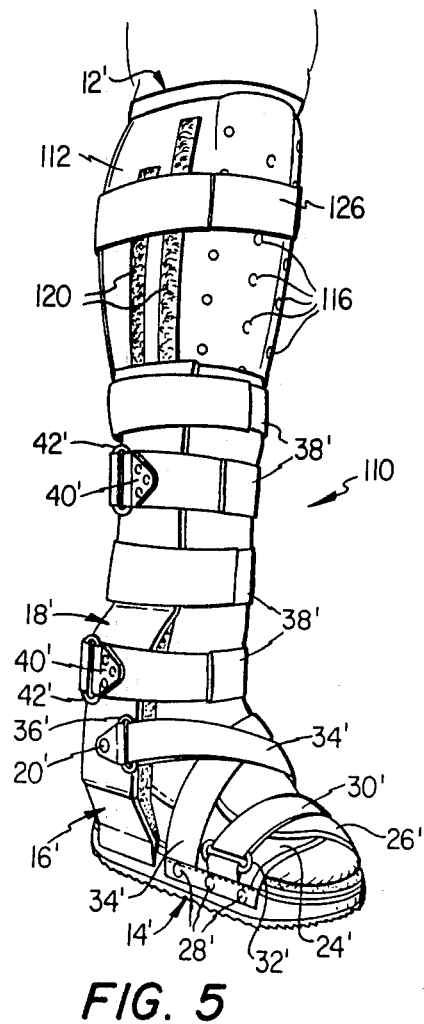
FIG. 5 is a perspective view of a brace for tibial fractures incorporating a second embodiment of the invention.

Referring now to the Drawings and particularly to FIGS. 1, 2 and 3 thereof, there is shown a removable ankle brace 10 comprising a first embodiment of the invention. The removable ankle brace 10 of the present invention incorporates numerous component parts which are substantially identical in construction and function to corresponding component parts of the Removable Ankle Brace disclosed and claimed in U.S. Pat. No. 4,378,793 granted to Donald M. Mauldin and Richard E. Jones, III on Apr. 5, 1983, the disclosure of which is incorporated herein by reference as if fully set forth herein.

A cuff 12 is secured around the leg of the patient prior to the mounting thereon of the remainder of the removable ankle brace 10. The cuff 12 is preferably formed from plastic foam, and may be provided with additional padding formed from plastic foam or other materials on the interior thereof, if desired. The cuff 12 further comprises conventional fastening means for securing the cuff on the leg of the patient. Preferably, the cuff 12 is provided with fasteners of the type sold under the trademark "VELCRO", and the foam material comprising the cuff 12 is of the type adapted for direct gripping engagement by the VELCRO fasteners thereof.

The removable ankle brace 10 further comprises a rigid shoe 14. Side members 16 extend upwardly from the rigid shoe 14 on opposite sides thereof. A side plate 18 is secured to each side member 16 by fasteners 20 which may comprise rivets or other conventional fasteners, and extends upwardly therefrom.

The rigid shoe 14 of the removable ankle brace 10 is provided with overlapping pads 24 and 26 which are secured to the opposite sides of the rigid shoe 14 by fasteners 28 which preferably comprise rivets. After the cuff 12 has been properly positioned on the lower leg of the patient the foot of the patient is located relative to the rigid shoe 14. Thereafter, a plurality of straps are utilized to secure the removable ankle brace on the lower leg and the foot of the patient and to assure that the proper positioning of the foot of the patient relative to the rigid shoe 14 is maintained. The straps of the removable ankle brace 10 are provided with suitable fastening means which preferably comprise VELCRO fasteners.

The retaining straps of the removable ankle brace 10 include a first strap 30 which is secured to one side of the rigid shoe 14 by the fasteners 28. The first strap 30 is extended through a ring 32 secured to the opposite side of the rigid shoe 14 by the fasteners 28 and is then doubled back upon itself and secured in place. A pair of second straps 34 are secured to the opposite sides of the rigid shoe 14 by the fasteners 28. The second straps 34 extend through rings 36 which are secured to the side plates 18 and to the side members 16 by the fasteners 20 and are then doubled back upon themselves and secured in place. A plurality of third straps 38 are each secured to one of the side plates 18 either by the fasteners 20 or by fasteners 40. The third straps 38 each have a ring 42 secured at one end thereof. In use, the third straps 38 are wrapped around the side plates 18 and the cuff 12 and are extended through their respective rings 42. The third straps 38 are then doubled back upon themselves and secured in place.

Figure 4:
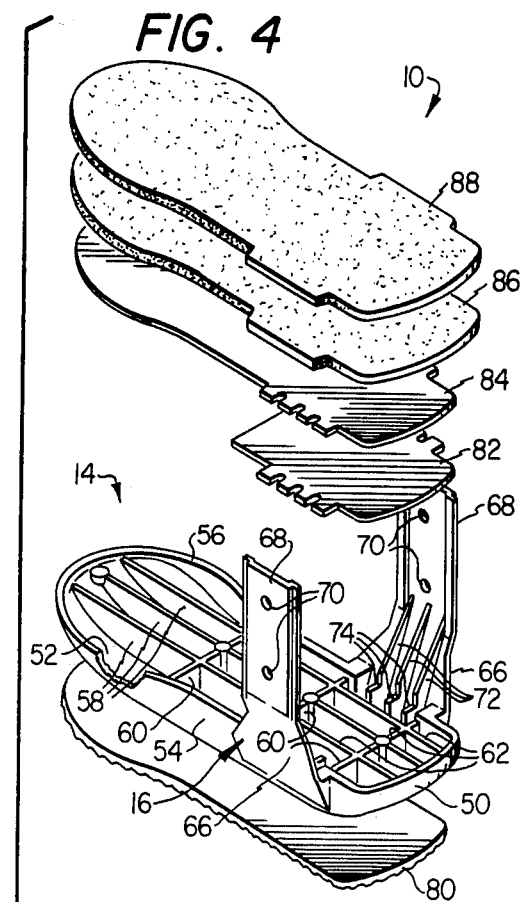
FIG. 4 is an exploded perspective view showing the construction of the removable ankle brace of FIG. 1.

Referring now to FIG. 4, the construction of the rigid shoe 14 of the removable ankle brace 10 is shown in greater detail. The rigid shoe 14 includes a molded plastic body portion 50. Although not critical to the practice of the invention, the molded plastic body portion 50 of the rigid shoe 14 is preferably formed from 6,6 nylon which is 20% glass filled.

The molded plastic body portion 50 includes an imperforate bottom wall 52. A side wall 54 extends around the periphery of the bottom wall 52 and has an upper edge 56. A plurality of longitudinally extending ribs 58 and a plurality of transversely extending ribs 60 extend upwardly from the bottom wall 52. The ribs 58 and 60 have upper edges 62 which define a plane positioned below the upper edge 56 of the side wall 54.

The side members 16 are formed integrally with the molded plastic body portion 50. The side members 16 each comprise first portions 66 extending angularly upwardly and outwardly from the side wall 54 of the molded body portion 50 and second portions 68 extending upwardly from the upper ends of the first portion 66 substantially parallel to the side wall 54. The second portions 68 of the side members 16 have apertures 70 formed therein for receiving the fasteners 20. Each side member 16 further includes a plurality of reinforcing ribs 72. The ribs 72 extend vertically upwardly from the bottom wall 52 along the interior of the side wall 54 of the molded plastic body portion 50 to edges 74 which are in the same plane as the upper edges 62 of the reinforcing ribs 58 and 60, and then extend further upwardly along the interior surfaces of the first portions 66 of the side members 16. The ribs 72 terminate at the point of intersection of the first and second portions 66 and 68 of the side members 16.

The integral construction of the molded plastic body portion 50 and the side members 16 of the removable ankle brace 10 comprise a very important feature of the invention. This construction assures that any possibility of relative movement between the side members 16 and the rigid shoe 14 is completely eliminated. In this manner the removable ankle brace 10 is adapted for long term, substantially maintenance free service.

The rigid shoe 14 further comprises a tread 80 which is secured to the underside of the bottom wall 52 of the molded plastic body portion 50 by means of a suitable adhesive. The tread 80 is formed from an elastomeric material such as natural or synthetic rubber, or from various plastic materials having similar characteristics. The lower surface of the tread 80 is corrugated so as to provide a nonslip surface. The tread 80 provides some resiliency, but does not alter the rigid nature of the rigid shoe 14.

The rigid shoe 14 further comprises a partial plastic layer 82 which is positioned on the upper edges 62 of the ribs 58 and 60 in the heel region of the shoe and a full plastic layer 84 which overlies the entirety of the molded plastic body portion 50 within the border defined by the upper edge 56 of the side wall 54. The full plastic layer 84 engages the partial plastic layer 82 in the heel region of the shoe and engages the upper edges 62 of the ribs 58 and 60 in the remainder of the shoe to define a planar surface which supports the foot of the patient. The use of such a planar surface is considered important in the practice of the invention in that it stabilizes the foot of the patient and thereby facilitates healing.

Dual layers of plastic foam 86 and 88 are secured on top of the plastic layer 84 to facilitate patient comfort. The use of the foam layers 86 and 88 does not alter the planar nature of the foot engaging surface of the rigid shoe 14.

Referring to FIG. 2, the molded plastic body portion 50 and the tread 80 define a substantially planar surface 90 extending rearwardly from a line 92 which extends transversely across the underside of the rigid shoe 14 and a curved surface 94 extending forwardly therefrom. The removable ankle brace 10 normally rests on the planar surface 90 so as to provide stability for the patient. However, during walking the transition line 92 between the planar surface 90 and the curved surface 94 defines a fulcrum. The metatarsal portion of the foot of the patient is located on the rigid shoe 14 forwardly of the fulcrum 92 so that as the weight of the patient is shifted forwardly in walking, the brace 10 pivots forwardly on the curved surface 94. In this manner the removable ankle brace 10 simulates a natural walking movement even though the foot of the patient is secured therein sufficiently to prevent any pivotal movement of the ankle whatsoever.

As is best shown in FIG. 3, each side plate 18 includes an attachment portion 100 which receives the second portion 68 of the associated side member 16 and which is secured thereto by means of the fasteners 20. A second portion 102 of the side plate 18 extends angularly upwardly and inwardly from the attachment portion 100, and a third portion 104 extends vertically upwardly from the upper end of the second portion 102. The third portions 104 of the side plates 18 substantially overlie and extend parallel to the side wall 54 of the molded plastic body portion 50, but are curved inwardly to facilitate snug engagement thereof with the calf of the patient. Strips of VELCRO material 106 are adhesively secured at the upper ends of the third portions 104 of the side plates 18 to facilitate the attachment of the cuff 12 thereto. Layers of foam padding 108 are secured on each side of the removable ankle brace 10 and extend upwardly along the upper region of the first portion 66 of each side member 16, along the entirety of the second portion 68 of the side member 16, and along the lower region of the second portion 102 of the side plate 18.

In the use of the removable ankle brace 10 the cuff 12 is first wrapped around the lower leg of the patient and is secured in place. The foot of the patient is then positioned on the planar upper surface afforded by the rigid shoe 14 with the metatarsal point of the foot positioned ahead of the fulcrum defined by the line 92. The overlapping pads 24 and 26 are folded over the foot of the patient, and the straps 30, 34 and 38 are then utilized to secure the removable ankle brace 10 to the foot and the lower leg of the patient. In this manner the foot and ankle of the patient are entirely stabilized. Nevertheless, the patient is able to walk comfortably because of the use of the planar surface 90, the fulcrum defined by the line 92 and the curved surface 94 on the underside of the rigid shoe 14.

Figure 6:
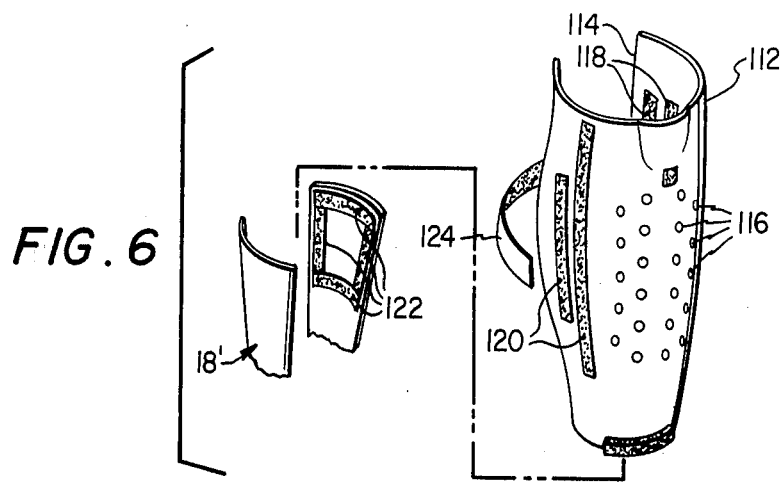
FIG. 6 is an exploded partial perspective view of the brace for tibial fractures of FIG. 5.

Referring to FIGS. 5 and 6, there is shown a brace for tibial fractures 110 comprising a second embodiment of the invention. The brace for tibital fractures 110 is similar in many respects to the Brace For Tibial Fractures disclosed and claimed in U.S. Pat. No. 4,414,965 granted to Donald M. Mauldin and Richard E. Jones, III on Nov. 15, 1983 the disclosure of which is incorporated herein by reference as if fully set forth herein.

The brace for tibial fractures 110 incorporates numerous component parts that are substantially identical in construction and function to component parts of the removable ankle brace 10 illustrated in FIGS. 1–4 inclusive, and described hereinabove in conjunction therewith. Such identical component parts are designated in FIGS. 5 and 6 with the same reference numerals utilized in the description of the removable ankle brace 10 but are differentiated therefrom by means of a prime (') designation.

The primary distinction between the removable ankle brace 10 and the brace for tibial fractures 110 comprises the fact that the brace for tibial fractures 110 is provided with an extension 112 to facilitate the use thereof in the treatment of tibial fractures. In order to accommodate the additional length afforded by the use of the extension 112 the brace for tibial fractures 110 is provided with a cuff 12' which is substantially longer than the cuff 12 of the removable ankle brace 10. Otherwise, the cuff 12' of the brace for tibial fractures 110 is identical in construction and function to the cuff 12 of the removable ankle brace 12.

Referring particularly to FIG. 6, the extension 112 comprises a sheet of plastic material which is formed into a cylindrical configuration. The edges of the sheet of plastic material define a slot 114 therebetween. The material utilized in the fabrication of the extension 112 is sufficiently flexible to allow the slot 114 to be opened wide enough to receive the leg of the patient. Flexure of the extension 112 is facilitated by a plurality of holes 116 formed in the plastic material at the front thereof.

Strips of VELCRO material 118 are secured to the interior of the extension 112 to secure the extension 112 in engagement with the cuff 12'. Strips of VELCRO material 120 are also secured to the exterior of the extension 112. The strips of VELCRO material 120 serve two purposes. First, the strips of VELCRO material 120 cooperate with strips of VELCRO material 118 secured to the interior surface of the side plates 18' to secure the extension 112 to the remainder of the brace for tibial fractures 110. Second, the strips of VELCRO material 120 cooperate with a strap 124 having VELCRO material on the interior thereof to secure the slot 14 in a closed condition after the extension 112 has been positioned on the leg of a patient. The extension 112 is further secured on the leg of the patient by a strap 126 which is secured to the extension 112 and which is provided with a ring similar to the ring 42'. In use, the strap 126 is wrapped around the extension 112 and is extended through the ring. Thereafter the strap 126 is doubled back upon itself and is secured in place.

The use of the brace for tibial fractures 110 is similar in many respects to the use of the removable ankle brace 10. First, the cuff 12' is wrapped around the leg of the patient and is secured in place. Next, the extension 112 is secured in place around the leg of the patient. Finally, the remainder of the brace for tibial fractures 110 is mounted on the lower leg and the foot of the patient and is secured in place by means of the straps 30', 34' and 38'.

Like the removable ankle brace 10, the brace for tibial fractures 110 is mounted on the leg and foot of the patient with the metataral point of the foot positioned ahead of the fulcrum defined by the line 92'. In this manner the patient is allowed to walk in a very natural fashion even though the foot, ankle and lower leg of the patient are entirely secured by the brace for tibial fractures 110.

Although preferred embodiments of the invention have been illustrated in the accompanying Drawings and described in the foregoing Detailed Description, it will be understood that the invention is not limited to the embodiments disclosed, but is capable of numerous rearrangements, modifications, and substitutions of parts and elements without departing from the spirit of the invention.

We claim:

1. A brace for treatment of tibial fractures comprising:

a rigid shoe including a planar upper surface member for engaging the sole of the patient's foot, side walls extending perpendicularly to the upper surface and downwardly therefrom, and an outer sole member comprising the lowermost surface of the shoe;

the outer sole of the shoe having a fulcrum, a planar first portion extending rearwardly from the fulcrum to the heel of the shoe and a second portion comprising a continuous curve extending from the fulcrum upwardly and forwardly to the toe of the shoe;

means for locating the foot of the patient on the planar upper surface of the shoe with the metatarsal point of the foot positioned forward of the fulcrum so that the shoe normally sets on the planar first portion of the outer sole and pivots about the fulcrum onto the curved second portion as the weight of the patient shifts forward of the metatarsal point of the foot;

said rigid shoe further comprising a molded plastic body portion having the planar upper surface member and the outer sole member secured thereto and molded plastic left and right side members formed integrally with the body portion and positioned on opposite sides of the shoe;

the side members each comprising a first portion extending from the side wall of the shoe angularly upwardly and outwardly with respect thereto and a second portion extending upwardly from the upper end of the second portion substantially parallel to the side wall of the shoe;

plastic side plates secured to the side members and each including an attachment portion secured to the second portion of its respective side member, a second portion extending from the upper end of the attachment portion angularly upwardly and inwardly with respect thereto, and a third portion extending upwardly from the upper end of the second portion generally parallel to the second portion of the side member and to the attachment portion of the side plate;

the third portion of each side plate positioned over the side wall of the shoe and being curved inwardly to conform to the calf of the patient;

each side member further including a layer of foam padding secured to the inside surface thereof and extending upwardly along the inner surfaces of the first and second portions of the side member;

an extension secured to the upper end of the third portion of the side plates and extending therefrom upwardly beyond the knee of the patient; and fastening means for securing the shoe, the side members and the extension in place relative to the leg of the patient.

2. The brace according to claim 1 further including a foam cuff dimensioned to surround the portion of the leg of the patient extending above and below the knee and means mounted on the inner surfaces of the extension for securing the cuff thereto.

3. The brace according to claim 1 wherein the fastening means comprises:

first strap means for connection between aligned points on the side walls of the shoe adjacent the toe thereof;

second strap means for connection between points on the side walls and points on the opposite side members;

said first and second strap means for securing the shoe to the foot of the patient;

third strap means for connection between aligned points on the side plates to secure the side plates to the calf of the patient; and fourth strap means for connection between aligned points on the extension to secure the extensions to the portion of the leg of the patient extending above and below the knee.

4. The brace according to claim 3 further including fasteners extending through the second portions of the side members and the attachment portions of the side plates for joining each side member, its corresponding side plate and the second strap means one to another.

5. The brace according to claim 1 further including plastic reinforcing members formed integrally with the body portion and the side members and extending along the inside surfaces of the side members from the lower ends of the second portions thereof to the body portion.

6. A removable ankle brace comprising:

a rigid shoe including a planar upper surface member for engaging the sole of the patient's foot, side walls extending perpendicularly to the upper surface and downwardly therefrom, and an outer sole member comprising the lowermost surface of the shoe;

the outer sole of the shoe having a fulcrum, a planar first portion extending rearwardly from the fulcrum to the heel of the shoe and a second portion comprising a continuous curve extending from the fulcrum upwardly and forwardly to the toe of the shoe;

means for locating the foot of the patient on the planar upper surface of the shoe with the metatarsal point of the foot positioned forward of the fulcrum so that the shoe normally sets on the planar first portion of the outer sole and pivots about the fulcrum onto the curved second portion as the weight of the patient shifts forward of the metatarsal point of the foot;

said rigid shoe further comprising a molded plastic body portion having the planar upper surface member and the outer sole member secured thereto and molded plastic left and right side members formed integrally with the body portion and positioned on opposite sides of the shoe;

the side members each comprising a first portion extending from the side wall of the shoe angularly upwardly and outwardly with respect thereto and a second portion extending upwardly from the upper end of the second portion substantially parallel to the side wall of the shoe;

plastic side plates secured to the side members and each including an attachment portion secured to the second portion of its respective side member, a second portion extending from the upper end of the attachment portion angularly upwardly and inwardly with respect thereto, and a third portion extending upwardly from the upper end of the second portion generally parallel to the second portion of the side member and to the attachment portion of the side plate;

the third portion of each side plate being positioned over the side wall of the shoe and being curved inwardly to conform to the calf of the patient;

each side member further including a layer of foam padding secured to the inside surface thereof and extending upwardly along the inner surfaces of the first and second portions of the side member; and fastening means for securing the shoe, the side members and the side plates in place relative to the leg of the patient.

7. The brace according to claim 6 further including a foam cuff dimensioned to surround the portion of the leg of the patient and means mounted on the inner surfaces of the side plates for securing the cuff thereto.

8. The brace according to claim 6 wherein the fastening means comprises:

first strap means for connection between aligned points on the side walls of the shoe adjacent the toe thereof;

second strap means for connection between points on the side walls and points on the opposite side members;

said first and second strap means for securing the shoe to the foot of the patient; and third strap means for connection between aligned points on the side plates to secure the side plates to the calf of the patient.

9. The brace according to claim 8 further including fasteners extending through the second portions of the side members and the attachment portions of the side plates for joining each side member, its corresponding side plate and the second strap means one to another.

10. The brace according to claim 6 further including plastic reinforcing members formed integrally with the body portion and the side members and extending along the inside surfaces of the side members from the lower ends of the second portions thereof to the body portion.

* * * * *